(12) United States Patent
Nagae

(10) Patent No.: US 9,367,945 B2
(45) Date of Patent: Jun. 14, 2016

(54) OBJECT INFORMATION ACQUISITION APPARATUS, DISPLAY METHOD, AND COMPUTER-READABLE MEDIUM STORING PROGRAM

(71) Applicant: CANON KABUSHIKI KAISHA, Tokyo (JP)

(72) Inventor: Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 45 days.

(21) Appl. No.: 13/972,176

(22) Filed: Aug. 21, 2013

(65) Prior Publication Data

US 2014/0063002 A1 Mar. 6, 2014

(30) Foreign Application Priority Data

Aug. 28, 2012 (JP) .................................. 2012-187619

(51) Int. Cl.

| A61B 8/00 | (2006.01) |
| G06T 15/00 | (2011.01) |
| G01S 7/52 | (2006.01) |
| G01S 15/89 | (2006.01) |
| G10K 11/34 | (2006.01) |
| A61K 8/46 | (2006.01) |
| A61B 8/08 | (2006.01) |

(52) U.S. Cl.
CPC ................. *G06T 15/00* (2013.01); *A61B 8/461* (2013.01); *A61B 8/469* (2013.01); *A61B 8/5207* (2013.01); *A61K 8/463* (2013.01); *G01S 7/52047* (2013.01); *G01S 7/52063* (2013.01); *G01S 15/8915* (2013.01); *G10K 11/346* (2013.01); *A61B 8/08* (2013.01)

(58) Field of Classification Search
None
See application file for complete search history.

(56) References Cited

U.S. PATENT DOCUMENTS

| 2002/0173721 A1* | 11/2002 | Grunwald et al. ............. 600/437 |
| 2006/0173319 A1* | 8/2006 | Sumi ............................. 600/437 |
| 2008/0171939 A1* | 7/2008 | Ishihara ....................... 600/449 |

(Continued)

FOREIGN PATENT DOCUMENTS

| CN | 101410061 A | 4/2009 |
| CN | 101416887 A | 4/2009 |

(Continued)

OTHER PUBLICATIONS

Sasso et al.,"Medical Ultrasound Imaging Using the Fully Adaptive Beamformer", IEEE International Conference on Acoustics, Speech and Signal Processing, 2005, pp. 489-492, Feb. 2005.

(Continued)

*Primary Examiner* — Kee M Tung
*Assistant Examiner* — Ryan M Gray
(74) *Attorney, Agent, or Firm* — Canon USA Inc., IP Division

(57) ABSTRACT

A display control unit included in an object information acquisition apparatus receives information about a depth range, subjected to display of a distribution related to acoustic characteristics, input by a user, and outputs, when the depth range is narrower than a predetermined range, image information for displaying an image of second distribution information subjected to adaptive signal processing in an area corresponding to the depth range or a combined image obtained by combining first distribution information subjected to addition processing with a predetermined weight and the second distribution information.

21 Claims, 9 Drawing Sheets

(56) References Cited

U.S. PATENT DOCUMENTS

| | | | |
|---|---|---|---|
| 2008/0269610 A1* | 10/2008 | Burla et al. | 600/447 |
| 2009/0088641 A1* | 4/2009 | Baba et al. | 600/455 |
| 2009/0299184 A1 | 12/2009 | Walker et al. | |
| 2011/0066032 A1* | 3/2011 | Vitek et al. | 600/459 |
| 2012/0022373 A1* | 1/2012 | Tateyama | G01S 7/52034 600/437 |
| 2012/0289835 A1* | 11/2012 | Hwang | 600/447 |
| 2014/0071792 A1* | 3/2014 | Yoo et al. | 367/103 |

FOREIGN PATENT DOCUMENTS

| | | | |
|---|---|---|---|
| JP | 7334665 A | | 12/1995 |
| JP | 9269370 A | | 10/1997 |
| JP | 2011005237 A | | 1/2011 |
| JP | 2012024133 A | | 2/2012 |
| KR | WO2012091280 | * | 5/2012 |
| WO | 2010100868 A1 | | 9/2010 |
| WO | 2012035723 A1 | | 3/2012 |
| WO | 2012/081709 A1 | | 6/2012 |

OTHER PUBLICATIONS

Taki et al.,"High Range Resolution Medical Acoustic Vascular Imaging with Frequency Domain Interferometry", 32nd Annual International Conference of the IEEE EMBS, 2010, pp. 5298-5301, Aug. 2010.

* cited by examiner

OBJECT INFORMATION ACQUISITION APPARATUS, DISPLAY METHOD, AND COMPUTER-READABLE MEDIUM STORING PROGRAM

BACKGROUND OF THE INVENTION

1. Field of the Invention

The present invention relates to an object information acquisition apparatus, a display method, and a computer-readable medium storing a program. In particular, the present invention relates to a technique for displaying distribution information acquired by transmitting elastic waves to an object and receiving reflected waves from the object.

2. Description of the Related Art

In the field of ultrasonography, which is an ultrasound-based imaging technique used for object information acquisition, an ultrasonograph is known to transmit ultrasonic waves (elastic waves) to an object. In response thereof, the ultrasonograph receives reflected waves reflected inside the object, and acquires an ultrasonic echo image, based on the pulse echo method. Japanese Patent Application Laid-Open No. 2012-24133 discusses an apparatus for generating an ultrasonic image (especially moving image) by applying delay and sum, envelope detection, etc., to a plurality of received signals acquired by receiving ultrasonic waves. With the apparatus discussed in Japanese Patent Application Laid-Open No. 2012-24133, when a user specifies an area to be enlarged as a Region Of Interest (ROI), an enlarged image of the specified area is displayed on a display unit. To optimize image quality, the user can specify whether to apply filtering to data of the enlarged image.

With the apparatus discussed in Japanese Patent Application Laid-Open No. 2012-24133, the displayed enlarged image is acquired by applying envelope detection to scanning line signals (echo data) having undergone delay and sum, as with the image before enlargement. However, an image acquired through such process is considered to provide limited visibility even after enlargement.

The user may specify an intra-object observation range in the depth direction (distance in the transmission direction of ultrasonic beams) as a similar operation to an enlarging operation. If the user specifies a depth range in this manner, the enlargement rate for image display changes according to the specified depth range and a display area in the screen of the display unit. Specifically, when the size of the display area is predetermined, specifying up to a shallow position as an observation range in the depth direction provides an intra-object image enlarged to a further extent than specifying up to a deep position. In this case, a similar problem to that in the enlarging operation arises, and an acquired image is considered to provide limited visibility depending on the specified depth range.

SUMMARY OF THE INVENTION

The present invention is directed to a technique for displaying on a display unit images having a higher resolution than those of conventional technology when a user specifies an observation range in the depth direction.

According to an aspect of the present invention, an object information acquisition apparatus includes a plurality of conversion elements configured to transmit elastic waves to an object, to receive reflected waves reflected at respective positions within the object, and to convert the reflected waves into a plurality of receiving signals, a fixed signal processing unit configured to apply addition with a fixed weight to the plurality of receiving signals, and to acquire a plurality of signals corresponding to the reflected waves from the respective positions within the object as scanning line signals to acquire first distribution information, an adaptive signal processing unit configured to apply to the plurality of receiving signals adaptive signal processing with a weight adaptively changing according to the receiving signals to acquire second distribution information, and a display control unit configured to input the first distribution information and the second distribution information, and to output image information for displaying on a display unit an image indicating a distribution related to acoustic characteristics within the object, wherein the display control unit receives information about a depth range, within the object subjected to display of a distribution related to the acoustic characteristics, input by a user, and outputs, when the depth range is narrower than a predetermined range, image information for displaying on the display unit an image of the second distribution information in an area corresponding to the depth range or a combined image obtained by combining the first distribution information and the second distribution information, as an image indicating the distribution related to the acoustic characteristics.

According to another aspect of the present invention, a display method displays an image indicating a distribution related to acoustic characteristics within an object by using distribution information acquired by an object information acquisition apparatus, wherein the acquired distribution information includes first distribution information acquired by applying addition with a fixed weight to receiving signals acquired by transmitting elastic waves to the object and receiving reflected waves reflected within the object, and acquiring a plurality of scanning line signals corresponding to reflected waves from respective positions within the object, and second distribution information acquired by applying to the plurality of receiving signals adaptive signal processing with a weight adaptively changing according to the receiving signals, wherein the display method includes receiving information about a depth range, within the object subjected to display of a distribution related to the acoustic characteristics, input by a user, and displaying, when the depth range is narrower than a predetermined range, an image of the second distribution information in an area corresponding to the depth range or the combined image obtained by combining the first distribution information and the second distribution information, as an image indicating the distribution related to the acoustic characteristics.

Further features of the present invention will become apparent from the following description of exemplary embodiments with reference to the attached drawings.

DESCRIPTION OF THE EMBODIMENTS

Figure 1:
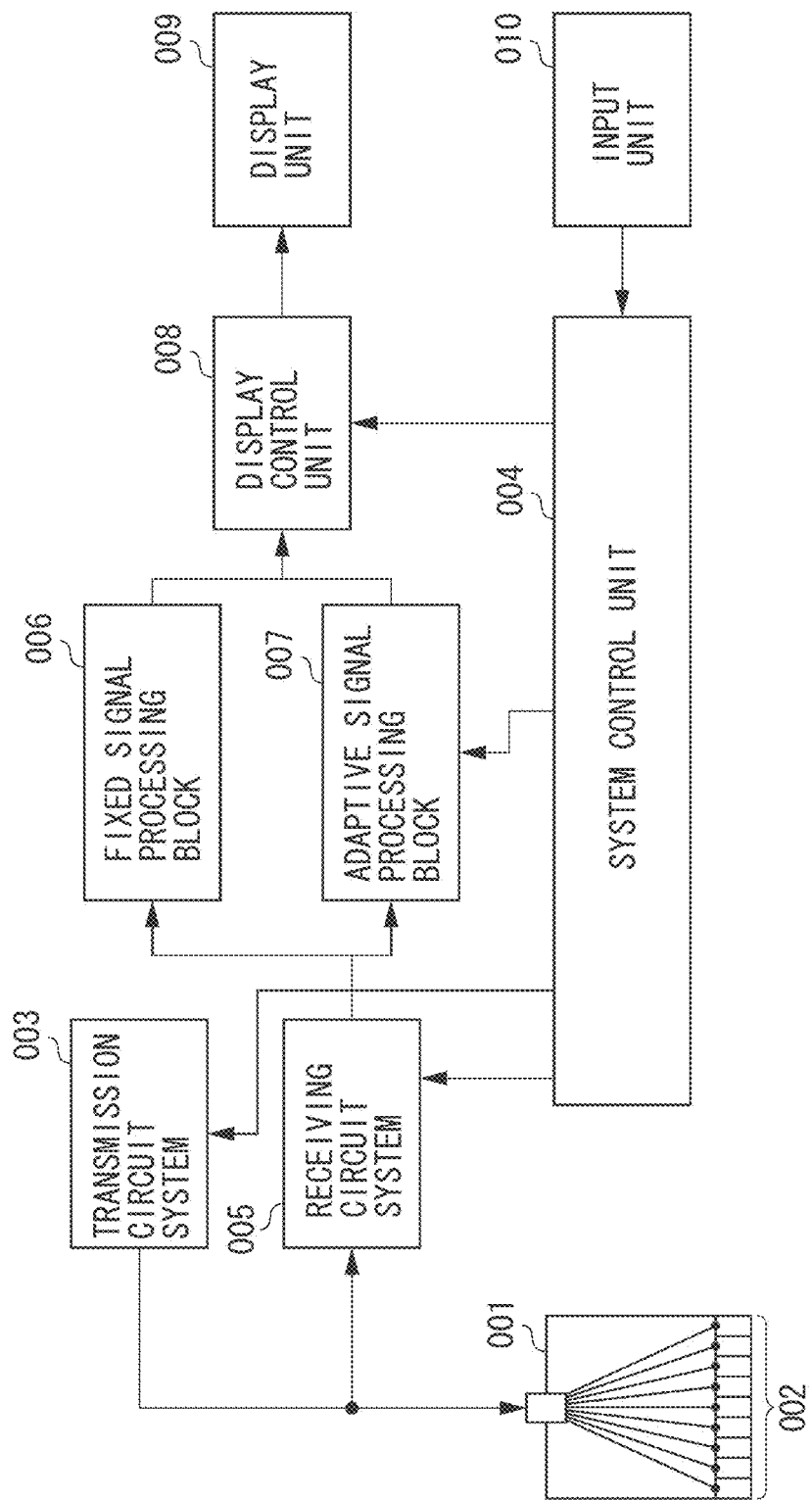
FIG. 1 schematically illustrates an overview of an object information acquisition apparatus according to a first exemplary embodiment of the present invention.

Various exemplary embodiments, features, and aspects of the invention will be described in detail below with reference to the drawings.

Hereinafter, identical elements are assigned the same reference numeral, and redundant descriptions will be omitted.

In the present invention, an elastic wave typically refers to an ultrasonic wave and includes what is called sound wave, ultrasonic wave, or acoustic wave. The object information acquisition apparatus according to the present invention includes an apparatus which transmits elastic waves to an object, receives reflected waves (reflected elastic waves) reflected inside the object, and acquires intra-object distribution information as image data. Acquired distribution information related to the acoustic characteristics within the object is information reflecting the acoustic impedance difference between intra-object tissues. In the present invention, scanning lines indicate virtual lines formed in the traveling direction of elastic waves transmitted from a probe.

A first exemplary embodiment of the present invention will be described below centering on a basic apparatus configuration and processing flow.

(Basic Configuration of Object Information Acquisition Apparatus)

A configuration of an object information acquisition apparatus according to the first exemplary embodiment will be described below with reference to FIG. 1. FIG. 1 schematically illustrates an overview of the object information acquisition apparatus according to the first exemplary embodiment. The object information acquisition apparatus (e.g., an ultrasonograph) according to the present exemplary embodiment includes a probe 001 having a plurality of conversion elements 002, a receiving circuit system 005, a transmission circuit system 003, a fixed signal processing block 006, an adaptive signal processing block 007, and a display control unit 008. The object information acquisition apparatus according to the present exemplary embodiment further includes a display unit 009, an input unit 010, and a system control unit 004.

The probe 001 is a transmitter/receiver device for transmitting ultrasound (elastic) waves to a plurality of positions within the object, and in response to the ultrasound waves it receives reflected waves. The probe 001 includes the plurality of conversion elements 002 (sensors) for converting elastic waves into electrical signals.

A transmission circuit system 003 is a transmission signal generation unit for generating, based on a control signal from the system control unit 004, a plurality of transmission signals having a delay time and an amplitude for each target position and each target direction. The plurality of conversion elements 002 converts the transmission signals into elastic waves. The probe 001 transmits the elastic waves to a non-illustrated object as elastic wave beams. The plurality of conversion elements 002 also receives elastic waves (reflected waves) reflected by intra-object subjects (reflective interfaces and reflectors), and converts the elastic waves into a plurality of receiving signals. The receiving circuit system 005 inputs the receiving signals.

The receiving circuit system 005 is a receiving signal processing unit for amplifying the plurality of receiving signals, and converting the receiving signals into a plurality of digital signals (digitized receiving signals). In the present exemplary embodiment, not only analog receiving signals output by the conversion elements 002 but also amplified and digitally converted signals are referred to as receiving signals. The fixed signal processing block 006 and the adaptive signal processing block 007 input the plurality of digital signals output from the receiving circuit system 005.

Figure 2:
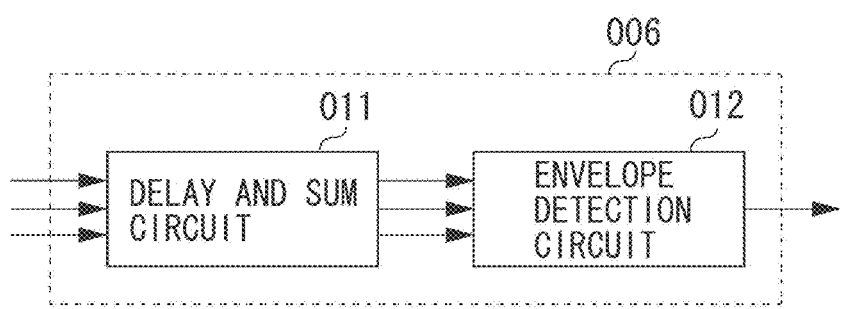
FIG. 2 schematically illustrates a configuration of a fixed signal processing block.

The fixed signal processing block 006 is equivalent to a fixed signal processing unit according to the present exemplary embodiment. FIG. 2 illustrates a configuration of the fixed signal processing block 006. In the fixed signal processing block 006, a delay and sum circuit 011 (delay and sum unit) applies delay processing to the plurality of digital signals according to transmission directions and positions of the elastic waves, and then applies sum processing to the plurality of digital signals having undergone the delay processing. Thus, delay and sum processing is performed on the plurality of digital signals. A plurality of scanning line signals is acquired by the delay and sum processing. The fixed signal processing block 006 may multiply each of the plurality of digital signals by a weight before applying delay and sum to the digital signals. Although the weight changes according to observation positions and transmission and reception conditions, a predetermined (fixed) weight is used in many cases. Delay and sum generates signals corresponding to the sound pressure of the reflected waves reflected at respective positions within the object, as scanning line signals. Then, the envelope detection circuit 012 (envelope detection unit) applies envelope detection to the plurality of scanning line signals to acquire first distribution information. The fixed signal processing block 006 outputs the acquired first distribution information to the display control unit 008.

The adaptive signal processing block 007 is equivalent to an adaptive signal processing unit according to the present exemplary embodiment. Adaptive signal processing adaptively changes relevant processing parameters according to the receiving signals. In particular, the Capon method (also referred to as Constrained Minimization of Power (CMP)), one of adaptive signal processing methods, is applied to a plurality of input signals so that the electric power is minimized with fixed sensitivity for the target directions and target positions. Such adaptive signal processing has an effect of improving the spatial resolution. The adaptive signal processing block 007 outputs as second distribution information the power distribution having an improved resolution in at least one of the depth direction and the direction perpendicular to the depth direction. The depth direction refers to the traveling direction of the elastic waves (ultrasonic beams) transmitted from the probe 001, and equals the scanning line direction. Adaptive signal processing will be described in detail below with reference to FIGS. 3A, 3B, and 3C.

In the present exemplary embodiment, each of the fixed signal processing block 006, the adaptive signal processing block 007, the display control unit 008, and the system control unit 004 is composed of a processing device, such as a central processing unit (CPU), a graphics processing unit (GPU), or a field programmable gate array (FPGA) chip. The display control unit 008 inputs the first distribution information from the fixed signal processing block 006, and the second distribution information from the adaptive signal processing block 007. The display control unit 008 outputs image information for displaying distribution information on the display unit 009. Based on the image information output from the display control unit 008, the display unit 009 displays an image indicating a distribution related to the acoustic characteristics within the object. The processing performed by the display control unit 008 will be described in detail below with reference to FIG. 4. The display control unit 008 applies various image processing, such as edge emphasis and contrast adjustment to image information of the first distribution information, image information of the second distribution information, and image information for a combination of the first and second distribution information, and outputs image information of luminance data.

The display unit 009 displays an image based on the image information input from the display control unit 008. The display unit 009 is a liquid crystal display (LCD), a cathode ray tube (CRT), or an organic electroluminescence (EL) display.

The input unit 010 is used by a user to specify a range in the depth direction (hereinafter referred to as a depth range). The input unit 010 is a pointing device, such as a mouse and a keyboard, a pen tablet, or a touchpad attached to the surface of the display unit 009. The input unit 010 may also be a dial or a button provided on the apparatus. The user may specify a depth range by using the input unit 010, referring to the image of the first distribution information displayed on the display unit 009. The display unit 009 and the input unit 010 may be connected to the object information acquisition apparatus according to the present exemplary embodiment, instead of being included in the object information acquisition apparatus according to the present exemplary embodiment. In depth range specification according to the present exemplary embodiment, the user may specify the distance from the surface of the object (zero distance) to specify a predetermined depth range from the surface of the object. Further, instead of specifying the depth from the surface of the object, the user may specify a depth range from a first predetermined depth to a second predetermined depth in the object.

(Details of Adaptive Signal Processing)

Figure 3A:
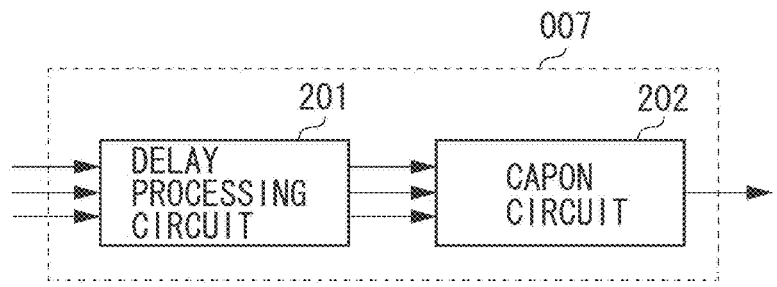
FIGS. 3A and 3B and 3C schematically illustrate different configurations of an adaptive signal processing block.
Figure 3B:
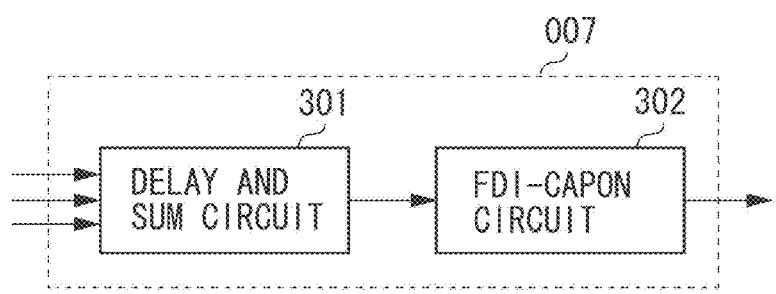
Figure 3C:
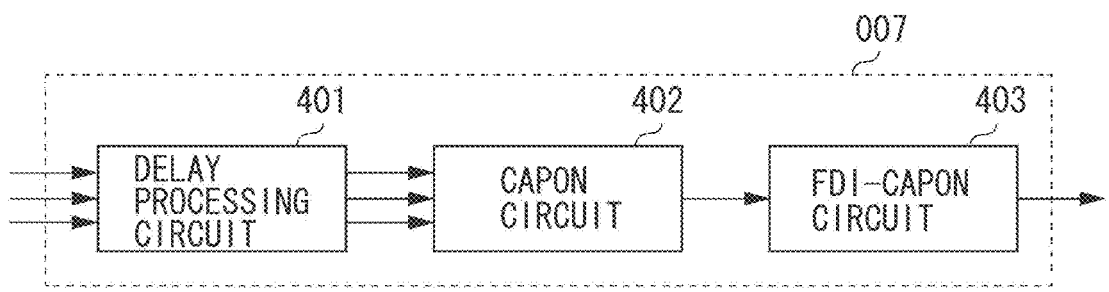

Processing performed by the adaptive signal processing block 007 according to the present exemplary embodiment will be described below. FIGS. 3A, 3B, and 3C illustrate three different configurations of the adaptive signal processing block 007. Example configurations of the adaptive signal processing block 007 according to the present exemplary embodiment will be described below with reference to FIGS. 3A, 3B, and 3C.

FIG. 3A illustrates a configuration of the adaptive signal processing block 007 for improving the resolution in the direction perpendicular to the depth direction, i.e., the traveling direction of the elastic waves (ultrasonic beams) transmitted from the probe 001. M. SASSO et al., Medical Ultrasound Imaging Using The Fully Adaptive Beamformer, Proc. Acoustics, Speech Signal Process. volume. 2, pp. 489-492 (March 2005) discusses a technique of such adaptive signal processing for improving the resolution in the direction perpendicular to the depth direction.

Processing performed when adaptive signal processing is applied to a plurality of receiving signals will be described below based on the Capon method.

Processing for calculating a correlation matrix based on the plurality of receiving signals will be described below. First of all, the delay processing circuit 201 applies the Hilbert transform and the delay processing (phasing processing) for respective target positions to the plurality of receiving signals output from the plurality of conversion elements 002. The receiving signals in the complex notation are calculated in this way. When the s-th sample of a signal obtained by processing a receiving signal from the k-th element is $x_k[s]$, an input vector $X[s]$ of the s-th sample is defined by the following formula:

$$X[s] = [x_1[s], x_2[s], \ldots, x_M[s]]^T \quad \text{Eq. (1)}$$

where M indicates the number of elements.

Then, a Capon circuit 202 (adaptive signal processing unit) calculates a correlation matrix $R_{xx}$ based on the input vector $X[s]$.

$$R_{xx} = E[X[s]X^H[s]] \quad \text{Eq. (2)}$$

$$= \begin{bmatrix} E[x_1[s]x_1^*[s]] & E[x_1[s]x_2^*[s]] & \ldots & E[x_1[s]x_M^*[s]] \\ E[x_2[s]x_1^*[s]] & E[x_2[s]x_2^*[s]] & \ldots & E[x_2[s]x_M^*[s]] \\ \vdots & \vdots & \ddots & \vdots \\ E[x_M[s]x_1^*[s]] & E[x_M[s]x_2^*[s]] & \ldots & E[x_M[s]x_M^*[s]] \end{bmatrix}$$

The superscript H indicates a complex conjugate transposition, and the superscript * indicates a complex conjugate. E[•] indicates processing for calculating a time average, i.e., processing for varying the sample number (s in this case) and calculating an average.

Then, to suppress the effect of a correlated interference wave which reaches the probe 001 from other than the target directions, the Capon circuit 202 applies the spatial averaging method to the correlation matrix $R_{xx}$ to obtain an average correlation matrix $R'_{xx}$.

$$R'_{xx} = \sum_{n=1}^{M-K+1} z_n R^n_{xx} \quad \text{Eq. (3)}$$

$R^n_{xx}$ indicates a partial matrix in the correlation matrix $R_{xx}$, moving along the diagonal elements of $R_{xx}$. Specifically, $R^n_{xx}$ is a matrix having a size of K×K, positioned so that the (n, n) element of $R_{xx}$ equals the first diagonal element of $R^n_{xx}$. $Z_n$ indicates a coefficient used when adding respective partial matrices, and is adjusted so that the sum total of $Z_n$ equals 1.

The Capon method obtains a complex weight for minimizing the output power under certain restriction conditions. The complex weight refers to a weight represented by a complex vector. With the Capon method, an optimum complex weight $W_{opt}$ for minimizing the output power, with the sensitivity for the receiving signals of the elastic waves from the target directions restrained to 1, can be calculated by the following formula:

$$W_{opt} = \gamma R'^{-1}_{xx} C, \quad \gamma = \frac{1}{C^H R'^{-1}_{xx} C} \quad \text{Eq. (4)}$$

C indicates a restriction vector, which varies according to the element position and target direction. However, when the phasing delay processing has been applied to the receiving signals, C may be a vector having all value of 1 with respect to the size (K in this case) of the average correction matrix.

An electric power $P_{min}$ can be calculated as follows based on the complex weight $W_{opt}$. The calculated electric power $P_{min}$ indicates distribution information (information about a distribution related to the acoustic characteristics) reflecting the acoustic impedance difference between intra-object tissues according to the present exemplary embodiment.

$$P_{min} = \frac{1}{2} \frac{1}{C^H R_{xx}^{\prime-1} C} \qquad \text{Eq. (5)}$$

The Capon circuit 202 can acquire a correlation matrix and further an average correction matrix based on the receiving signals, and, by using an inverse matrix, acquire a complex weight and a power distribution by using the complex weight. The complex weight and the electric power by using the complex weight are a complex weight and an electric power when the sensitivity is set to 1 for signals of the elastic waves from the target directions, and signals of the elastic waves reaching from other directions are suppressed. In other words, the Capon method enables selectively extracting signals of the elastic waves from the target directions, resulting in an improved spatial resolution in the direction perpendicular to the depth direction.

The electric power can also be calculated by applying QR decomposition and backward substitution to the average correction matrix, without directly obtaining an inverse matrix. The adaptive signal processing block 007 applies to the plurality of receiving signals in this way adaptive signal processing (using the Capon method) with a weight adaptively changing according to the receiving signals. As a result, the adaptive signal processing block 007 outputs a power distribution (equivalent to the second distribution information) having an improved spatial resolution in the direction perpendicular to the depth direction.

A second exemplary configuration of the adaptive signal processing block 007 will be described below with reference to FIG. 3B.

FIG. 3B illustrates a configuration of the adaptive signal processing block 007 for improving the resolution in the depth direction, i.e., the traveling direction of the elastic waves (ultrasonic beams) transmitted from the probe 001. As a technique for improving the spatial resolution in the depth direction, adaptive signal processing is combined with the Frequency Domain Interferometry (FDI) method. Hirofumi Taki, Kousuke Taki, Takuya Sakamoto, Makoto Yamakawa, Tsuyoshi Shiina and Toru Sato: Conf Proc IEEE Eng Med Biol Soc. 2010; 1: 5298-5301 discusses a technique in which the FDI method and the Capon method (adaptive signal processing) are applied.

The FDI method decomposes receiving signals into frequency components, and varies the phase of the decomposed signals according to the target positions to presume the received electric power at the target positions. Phase variation can be predetermined based on the product of the distance from a certain reference position to the target positions and the number of waves corresponding to the frequency.

Specifically, a method combining the FDI method and adaptive signal processing will presume the received electric power at the target positions by applying phase variation and weight calculated for each signal through adaptive signal processing, instead of predetermined fixed phase variation and weight, to receiving signals decomposed into frequency components.

When applying the frequency averaging technique to receiving signals of elastic waves having a wide frequency band as with pulse waves, signal whitening is desirably applied to the receiving signals based on a reference signal.

Referring to FIG. 3B, the delay and sum circuit 301 (delay and sum unit) applies the delay processing to a plurality of digital signals according to the transmission directions and positions of the elastic waves, and applies delay and sum to the plurality of digital signals having undergone the delay processing. Similar to the delay and sum in the fixed signal processing block 006, the delay and sum in the adaptive signal processing block 007 generates signals corresponding to the sound pressure of the reflected waves reflected at respective positions within the object, as scanning line signals.

Then, an FDI-Capon circuit 302 (FDI adaptive processing unit) receives as input signals the plurality of scanning line signals output from the delay and sum circuit 301. Then, the FDI-Capon circuit 302 extracts signals for the time interval of one unit of processing, i.e., the processing range, based on the plurality of scanning line signals.

Then, the FDI-Capon circuit 302 applies the Fourier transform to the extracted signals to decompose the signals into frequency components ($X_{s1}$, $X_{s2}$, $X_{s3}$, . . . , and $X_{sN}$). In the meantime, the FDI-Capon circuit 302 inputs at least one reference signal from a reference signal storage unit (not illustrated). Then, the FDI-Capon circuit 302 applies the Fourier transform to the reference signal to decompose the reference signal into frequency components ($X_{r1}$, $X_{r2}$, $X_{r3}$, . . . , $X_{rN}$).

Then, the FDI-Capon circuit 302 performs whitening represented by the following formula:

$$X_{wk} = \frac{X_{sk} X_{rk}^*}{|X_{rk}|^2 + \eta} \qquad \text{Eq. (6)}$$

$X_{wk}$ (k=1, 2, . . . , N) indicates frequency components after whitening, $\eta$ indicates a minute amount for stabilization of calculation, and * indicates a complex conjugate. Then, the FDI-Capon circuit 302 calculates a correlation matrix R by using a vector Xf having frequency components having undergone whitening.

$$Xf = [X_{w1}, X_{w2}, \ldots, X_{wN}]^T$$

$$R = Xf Xf^{T*} \qquad \text{Eq. (7) and (8)}$$

where T indicates transposition. The correlation matrix R is a matrix having a size of N×N.

Then, the FDI-Capon circuit 302 extracts partial matrices from the correlation matrix R, and applies the frequency averaging technique to the partial matrices for averaging.

$$R' = \frac{1}{M} \sum_{m=1}^{M} R_m \qquad \text{Eq. (9) and}$$

$$R_{mij} = X_{W(i+m-1)} X_{W(j+m-1)}^* \qquad (10)$$

R' indicates a frequency average correction matrix, $R_m$ indicates a partial matrix of the correlation matrix R, and $R_{mij}$ indicates elements of $R_m$. Thus, the FDI-Capon circuit 302 calculates the frequency average correction matrix R'.

Then, the FDI-Capon circuit 302 inputs the restriction vector C. The restriction vector C varies according to a position r within the processing range, and is defined by the following formula.

$$C = [\exp(jk_1 r), \exp(jk_2 r), \ldots, \exp(jk_{N-M+1} r)]$$

The FDI-Capon circuit 302 calculates a power distribution P(r) in the processing range based on the frequency average correction matrix R' and the restriction vector C. The calculated power distribution P(r) indicates distribution information reflecting the acoustic impedance difference between intra-object tissues (information about the distribution related to the acoustic characteristics) according to the present exemplary embodiment.

$$P(r) = \frac{1}{C^T * (R' + \eta' E)^{-1} C}$$ Eq. (11)

η'E indicates a diagonal matrix added to stabilize the inverse matrix calculation.

In the present exemplary embodiment, the adaptive signal processing block 007 applies the FDI method and adaptive signal processing (based on the Capon method) to the plurality of receiving signals in this way. As a result, the adaptive signal processing block 007 outputs a power distribution (equivalent to the second distribution information) with an improved resolution in the depth direction.

A third exemplary configuration of the adaptive signal processing block 007 will be described below with reference to FIG. 3C. A delay processing circuit 401 applies the Hilbert transform and the delay processing for respective target positions to the plurality of receiving signals output from the plurality of conversion elements 002, and outputs digital signals. A Capon circuit 402 inputs the digital signals having undergone the delay processing, and applies the Capon processing to the digital signals. The Capon circuit 402 performs similar processing to the above-described processing (redundant descriptions will be omitted), and eventually outputs a signal Y[s] calculated by the following formula. X'[s] indicates a vector extracted from the input vector X[s] of the s-th sample, fitting the size of the complex weight $W_{opt}$.

$$Y[s] = W_{opt}^H X'[s]$$ Eq. (12)

The output Y[s] holds phase information of the reflected waveforms for respective target positions, enabling performing subsequent FDI-Capon processing. The FDI-Capon circuit 302 applies the FDI-Capon processing to the input signal Y[s], and outputs a power distribution.

Performing such processing enables acquiring a power distribution with improved resolutions in the depth direction and in the direction perpendicular to the depth direction.

Although the processing of the Capon method has specifically been described as an example of adaptive signal processing, similar effects of the present invention can also be obtained by applying other adaptive signal processing, such as the MUSIC method and the ESPRIT method.

(Display Method)

Figure 4:
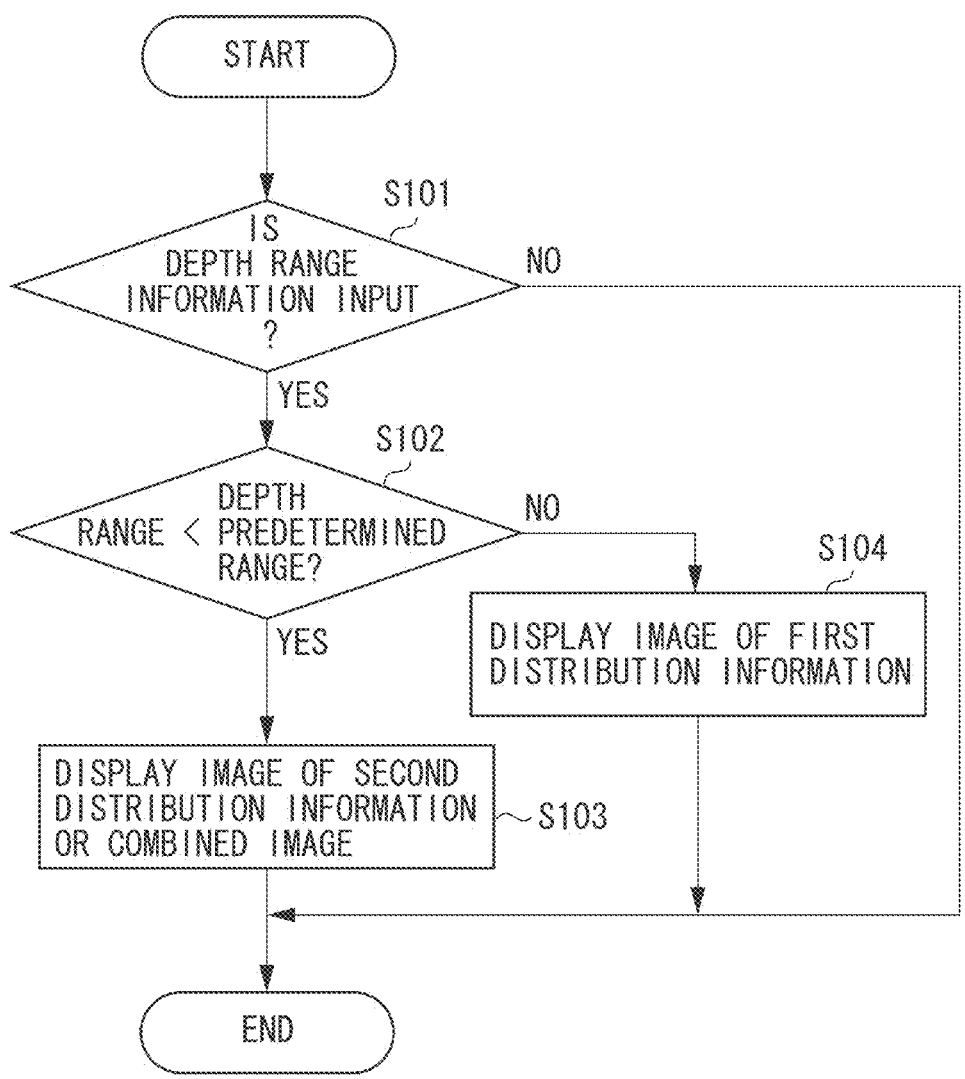
FIG. 4 is a flowchart illustrating processing of a display method according to the first exemplary embodiment.

Processing performed by a display method according to the present exemplary embodiment will be described below with reference to FIG. 4. FIG. 4 is a flowchart illustrating the display method according to the present exemplary embodiment.

In step 101, the display control unit 008 determines whether a depth range specification (depth range information) is input by the user. The user can specify a depth range to be observed, by using the input units 010, such as a mouse. The system control unit 004 inputs specified depth range information from the input unit 010, and outputs the specified depth range information to the display control unit 008 as depth range information from the user. As described above, the depth range may be the range from the surface of the object (zero distance) to a predetermined depth, or the range from the first predetermined depth to the second predetermined depth in the object. The display control unit 008 determines the display enlargement rate based on the relation between the depth range input by the user and the size of a display area for displaying object information in the screen of the display unit 009. The display enlargement rate refers to the ratio of the size of a displayed ultrasonic image in the observation range to the actual size of the intra-object observation range.

When depth range information is input (YES in step S101), then in step S102, the display control unit 008 determines whether the input depth range is narrower than a predetermined range. The predetermined range for comparison may be predetermined for each apparatus or arbitrarily set by the user.

When the input depth range is narrower (shallower) than the predetermined depth (YES in step S102), then in step 103, the display control unit 008 outputs to the display unit 009 image information for displaying the image of the second distribution information in an area corresponding to the input depth range or the combined image obtained by combining the first distribution information and the second distribution information, and the display unit 009 displays the image based on the input image information.

When the input depth range is wider (deeper) than the predetermined depth (NO in step S102), then in step 104, the display control unit 008 outputs to the display unit 009 image information for displaying the image of the first distribution information in an area corresponding to the input depth range, and the display unit 009 displays the image based on the input image information.

The following describes in detail the relation between the depth range input by the user and the size of the display area according to the present exemplary embodiment. The present exemplary embodiment will be described below centering on a case where, in step S103, the image of the second distribution information is displayed as an image in an area corresponding to the input depth range.

Figure 5:
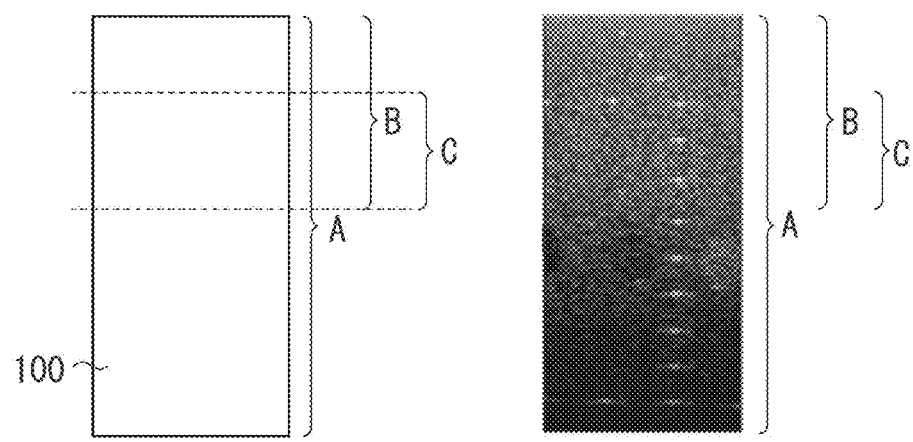
FIG. 5 schematically illustrates an exemplary depth specification according to the first exemplary embodiment.
Figure 6A:
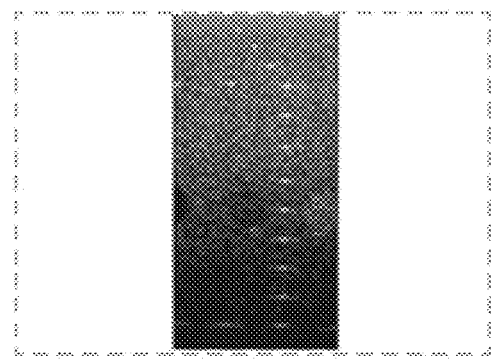
FIGS. 6A, 6B, and 6C illustrate example image display according to the first exemplary embodiment.
Figure 6B:
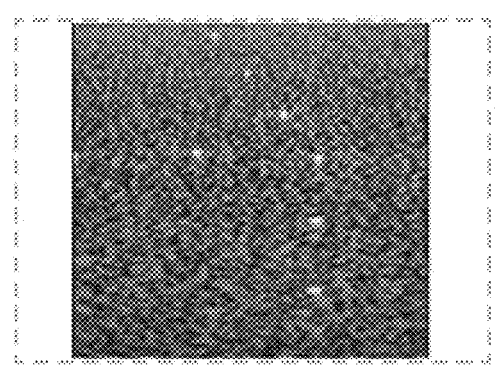
Figure 6C:
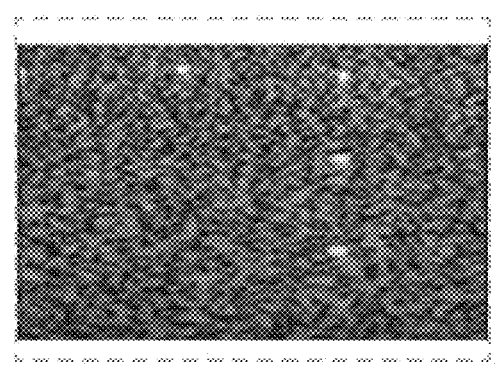

FIG. 5 illustrates an example of a specified depth range. Referring to FIG. 5, the left-hand side drawing illustrates three example ranges A, B, and C in the depth direction in an object 100, and the right-hand side image is the corresponding image of the first distribution information in the object 100. FIGS. 6A, 6B, and 6C illustrate example cases where images for areas corresponding to the depth ranges A, B, and C are displayed in the display area. FIG. 6A illustrates the image in an area corresponding to the depth range A. FIG. 6B illustrates the image in an area corresponding to the depth range B. FIG. 6C illustrate the image in an area corresponding to the depth range C. As the predetermined range to be used as a threshold value for the depth range (refer to step S102 in FIG. 4), a half range of the depth of the object 100 (assumed to be X mm) illustrated in FIG. 5 is assumed to be preset in the apparatus.

A case where the user specifies the depth range A illustrated in FIG. 5 will be described below. Since the depth range A is wider (deeper) than the predetermined range X mm, the processing proceeds to step S104. Then, the image of the first distribution information is displayed as an image indicating a distribution related to the acoustic characteristics within the object, as illustrated in FIG. 6A. Since the depth range A is larger than X mm, the display enlargement rate is not large when the entire image in the depth range A in the depth direction is displayed in the display area. Therefore, when displaying the depth range A, it is useful to display the image of the first distribution information in the area corresponding to the depth range A since the resolution of the image of the first distribution information (normal B mode image) is acceptable.

A case where the user specifies the depth range B will be described below. Since the depth range B is narrower (shallower) than the predetermined range X mm, the processing proceeds to step S103. Then, the image of the second distribution information in the area corresponding to the depth range B is displayed as an image indicating a distribution related to the acoustic characteristics within the object, as illustrated in FIG. 6B. Since the depth range B is narrower than X mm, the display enlargement rate is large because of the relation with the size of display area. Therefore, when displaying the depth range B, it is useful to display the image of the second distribution information having a high resolution to improve the visibility. The image of the second distribution information illustrated in FIG. 6B was acquired by performing the Capon method (example in FIG. 3A) as adaptive signal processing.

Figure 7A:
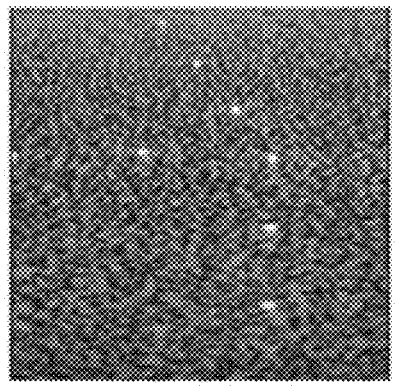
FIGS. 7A and 7B illustrate an image of first distribution information and an image of second distribution information displayed for comparison according to the first exemplary embodiment.
Figure 7B:
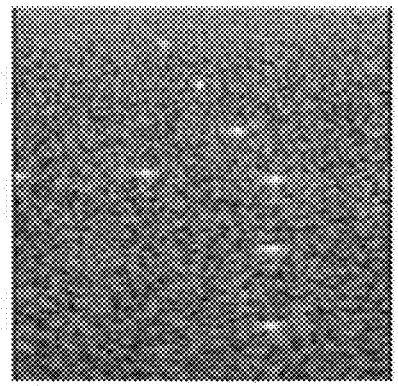

An image according to the present exemplary embodiment in the depth range B will be compared with an image not according to the present exemplary embodiment. FIG. 7A illustrates the image of the second distribution information acquired by performing the Capon method. FIG. 7B illustrates the image of the first distribution information which is a normal B mode image. Both of these images indicates the same area corresponding to the depth range B. As illustrated in FIG. 7A, depending on the display enlargement rate, simply displaying the image of the first distribution information degrades the visibility because of a low resolution. However, an enlarged version of the image of the second distribution information acquired through adaptive signal processing provides an improved resolution.

A case where the user specifies the depth range C will be described below. Since the depth range C is narrower than the predetermined range X mm, the processing proceeds to step S103, as with the case of the depth range B. Specifically, the image of the second distribution information in the area corresponding to the depth range C is displayed as an image indicating a distribution related to the acoustic characteristics within the object, as illustrated in FIG. 6C.

In the present exemplary embodiment, as described above, the display control unit 008 determines the display enlargement rate based on the relation between the depth range input by the user and the size of the display area in the screen of the display unit 009. Depending on the display enlargement rate, the display control unit 008 determines one of the image of the first distribution information, the image of the second distribution information, and the combined image obtained by combining the first distribution information and the second distribution information as an image to be displayed.

In the present exemplary embodiment, when the image in an area corresponding to the depth range is displayed, it is desirable to display a thumbnail for the image of the first distribution information in the same screen. In this case, the image of the first distribution information displays an area in a wide range including the area corresponding to the depth range.

Figure 8:
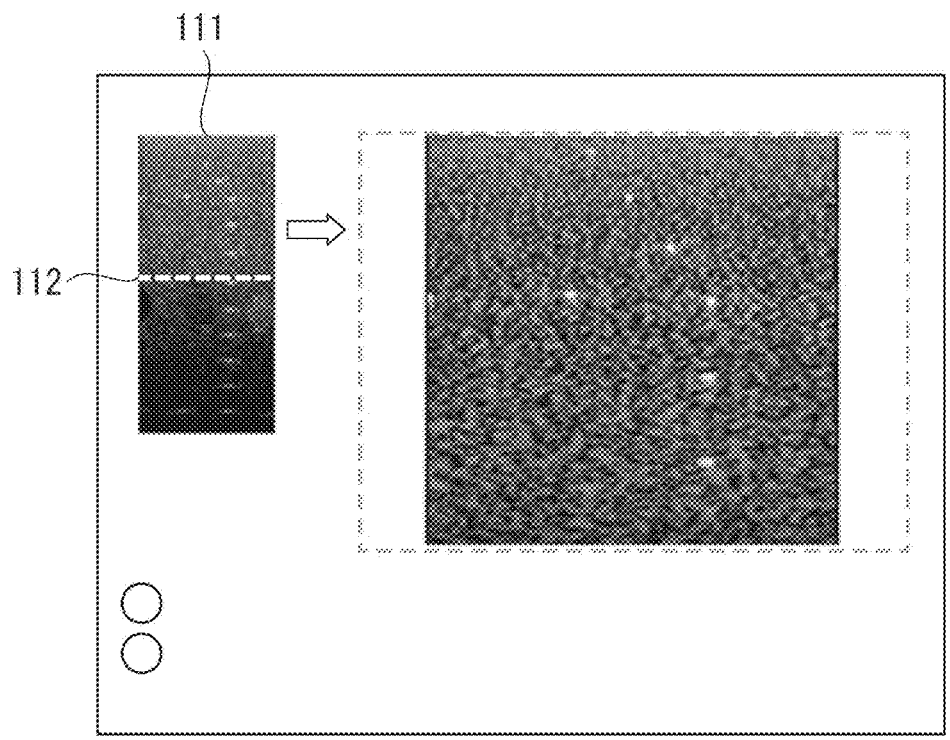
FIG. 8 schematically illustrates an example screen displayed on a display unit according to the first exemplary embodiment.

FIG. 8 illustrates an example display according to the present exemplary embodiment. Referring to the display screen illustrated in FIG. 8, the right-hand side image is the image in the area corresponding to the depth range (in this example, the image of the second distribution information in the area corresponding to the depth range B illustrated in FIG. 5), and the upper left image is a thumbnail image 111.

The image of the first distribution information displayed as the thumbnail image 111 includes at least the area corresponding to the depth range specified by the user, and can display an area in the range acquirable through ultrasonic wave transmission and reception (the image of the range illustrated as the right-hand side image in FIG. 5).

When displaying a thumbnail, it is desirable to display in the thumbnail image 111 a guide for indicating the area corresponding to the depth range specified by the user. In the thumbnail image 111 in FIG. 8, a dotted line is displayed as a guide 112 for indicating the area corresponding to the depth range. As with this dotted line, displaying a guide for indicating the specified depth range in the thumbnail image is desirable since the guide makes it easier for the user to grasp the depth range corresponding to the displayed image.

In the present exemplary embodiment, upon reception of the information about the depth range input by the user, the display control unit 008 can also turn OFF the above-described mode of the display processing flow illustrated in FIG. 4. Specifically, it is desirable that the display control unit 008 is capable of selectively executing the mode (first mode) for displaying the image of the second distribution information corresponding to the depth range or the combined image when the depth range is narrower than a predetermined range, and the mode (second mode) for displaying the image of the first distribution information regardless of the depth range. In the second mode, upon reception of the information about the depth range input by the user, the display control unit 008 displays the image of the first distribution information in the area corresponding to the depth range.

It is desirable that the first and second modes are selectable based on an input by the user via the input unit 010, such as a selector button or a switch. Mode selection in this way enables the user to change the image to be displayed by user preferences, further improving the user-friendliness.

A second exemplary embodiment of the present invention is characterized in displaying the combined image obtained by combining the first distribution information and the second distribution information in an area corresponding to the above-described depth range when the depth range input by the user is narrower than the predetermined range. Other processing is similar to that according to the first exemplary embodiment. An object information acquisition apparatus according to the present exemplary embodiment has a similar configuration to that of the object information acquisition apparatus illustrated in FIG. 1. Since the overview of the display method is basically the same as the processing flow described with reference to FIG. 4, the following describes only display processing different from that according to the first exemplary embodiment.

In the present exemplary embodiment, upon reception of the information about the depth range input by the user, the display control unit 008 displays in step S103 (FIG. 4) the combined image obtained by combining the first distribution information and the second distribution information in an area corresponding to the above-described depth range. The combination rate for the image of the first distribution information and the image of the second distribution information may be predetermined, such as 50:50, or arbitrarily set by the user. The combination rate may be changed with the depth range.

Figure 9:
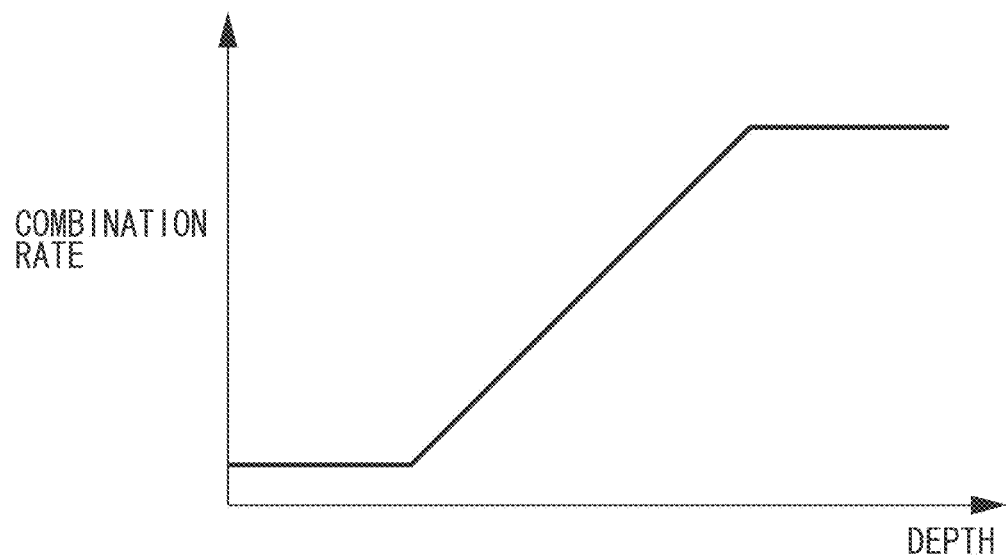
FIG. 9 illustrates a relation between the depth and the combination rate according to a second exemplary embodiment of the present invention.

FIG. 9 illustrates an example relation between the depth range and the combination rate. Referring to FIG. 9, when the depth range is below a first predetermined value, the display control unit 008 maintains constant the combination rate for the first and second distribution information. In this case, because of a narrow depth range, the combination rate for the image of the second distribution information is high (i.e., the ratio of the image of the first distribution information is low, and the ratio of the image of the second distribution information is high in the combined image). Then, when the depth range is higher than the first predetermined value and lower than a second predetermined value, the display control unit 008 decreases the combination rate for the image of the second distribution information (increases the ratio of the image of the first distribution information, and decreases the image of the second distribution information in the combined image) with increasing depth range. When the depth range is equal to or higher than the second predetermined value, the display control unit 008 maintains constant the combination rate for the first and second distribution information. In this case, because of a wide depth range, the display control unit 008 decreases the combination rate for the image of the second distribution information.

Changing the combination rate according to the depth range in this way allows the user to more smoothly switch between the first and second distribution information without feeling odd, possibly improving the user operability.

According to the exemplary embodiments of the present invention, displaying an image acquired through adaptive signal processing enables displaying an image having a higher resolution as an image in an area corresponding to a specified depth range.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-187619 filed Aug. 28, 2012, which is hereby incorporated by reference herein in its entirety.

What is claimed is:

1. An object information acquisition apparatus comprising:
a plurality of conversion elements configured to transmit elastic waves to an object, to receive reflected waves reflected at respective positions within the object, and to convert the reflected waves into a plurality of receiving signals;
a fixed signal processing unit configured to apply addition with a predetermined weight to the plurality of receiving signals to acquire first distribution information;
an adaptive signal processing unit configured to apply to the plurality of receiving signals adaptive signal processing with a weight adaptively changing according to the receiving signals to acquire second distribution information; and
a display control unit to which the first distribution information and the second distribution information is input, and configured to output image information for displaying on a display unit an image indicating a distribution related to acoustic characteristics within the object,
wherein the display control unit receives information about a user-input depth range, within the object subjected to display of a distribution related to the acoustic characteristics, and outputs, when the depth range is narrower than a predetermined range, image information for displaying on the display unit an image of the second distribution information or a combined image obtained by combining the first distribution information and the second distribution information for an area corresponding to the depth range.

2. The object information acquisition apparatus according to claim 1, wherein the display control unit is capable of selectively executing:
a first mode in which, upon reception of the information about the depth range, image information for displaying the image of the second distribution information or the combined image for the area corresponding to the depth range is output when the depth range is narrower than the predetermined range; and
a second mode in which, upon reception of the information about the depth range, image information for displaying an image of the first distribution information in the area corresponding to the depth range is output.

3. The object information acquisition apparatus according to claim 1, wherein, upon reception of the information about the depth range, the display control unit outputs image information for displaying an image of the first distribution information for the area corresponding to the depth range when the depth range is equal to or wider than the predetermined range.

4. The object information acquisition apparatus according to claim 1, wherein the display control unit determines a display enlargement rate for the distribution related to the acoustic characteristics based on a relation between the depth range input by the user and a display area in a screen of the display unit for displaying the distribution related to the acoustic characteristics.

5. The object information acquisition apparatus according to claim 1, wherein, when displaying the image of the second distribution information or the combined image for the area corresponding to the depth range, the display control unit displays an image of the first distribution information for a range including at least the area corresponding to the depth range, and a guide for indicating the area corresponding to the depth range in the image of the first distribution information in the range.

6. The object information acquisition apparatus according to claim 1, wherein the adaptive signal processing unit applies processing to the plurality of receiving signals so that electric power is minimized with fixed sensitivity for target directions.

7. The object information acquisition apparatus according to claim 1, wherein the adaptive signal processing unit applies processing to the plurality of receiving signals so that electric power is minimized with fixed sensitivity for target positions in a depth direction.

8. The object information acquisition apparatus according to claim 1, wherein the display control unit outputs, when the depth range is narrower than the predetermined range, image information for displaying on the display unit the combined image as the distribution related to the acoustic characteristics, and changes a combination rate for the first distribution information and the second distribution information according to the depth range.

9. A display method for displaying on a display unit an image indicating a distribution related to acoustic characteristics within an object by using distribution information acquired by an object information acquisition apparatus, wherein the acquired distribution information includes:

first distribution information acquired by applying addition with a predetermined weight to a plurality of receiving signals acquired by transmitting elastic waves to an object and receiving reflected waves reflected in the object; and second distribution information acquired by applying to the plurality of receiving signals adaptive signal processing with a weight adaptively changing according to the receiving signals, wherein the display method comprises:

receiving information about a user-input depth range, within the object subjected to display of a distribution related to the acoustic characteristics; and displaying, when the depth range is narrower than a predetermined range, an image of the second distribution information or a combined image obtained by combining the first distribution information and the second distribution information for an area corresponding to the depth range.

10. The display method according to claim 9, further comprising:

selectively executing the following modes:

a first mode in which, upon reception of the information about the depth range, when the depth range is narrower than the predetermined range, the image of the second distribution information or the combined image for the area corresponding to the depth range is displayed; and a second mode in which, upon reception of the information about the depth range, an image of the first distribution information in the area corresponding to the depth range is displayed.

11. The display method according to claim 9, further comprising:

displaying, when the depth range is equal to or wider than the predetermined range, an image of the first distribution information for the area corresponding to the depth range.

12. The display method according to claim 9, further comprising:

determining a display enlargement rate for the distribution related to the acoustic characteristics based on a relation between the depth range input by the user and the display area in the screen of the display unit for displaying the distribution related to the acoustic characteristics.

13. The display method according to claim 9, further comprising:

displaying, when displaying the image of the second distribution information or the combined image for the area corresponding to the depth range, an image of the first distribution information in a range including at least the area corresponding to the depth range, and a guide for indicating the area corresponding to the depth range in the image of the first distribution information.

14. The display method according to claim 9, wherein the second distribution information is distribution information acquired by applying adaptive signal processing to the plurality of receiving signals so that electric power is minimized with fixed sensitivity for target directions.

15. The display method according to claim 9, wherein the second distribution information is distribution information acquired by applying adaptive signal processing to the plurality of receiving signals so that electric power is minimized with fixed sensitivity for target positions in a depth direction.

16. The display method according to claim 9, further comprising:

displaying, when the depth range is narrower than the predetermined range, the combined image as the distribution related to the acoustic characteristics; and changing a combination rate for the combined image for the first and second distribution information according to the depth range.

17. A non-transitory computer-readable storage medium storing a program that causes a computer to execute a display method for displaying on a display unit an image indicating a distribution related to acoustic characteristics within an object by using distribution information acquired by an object information acquisition apparatus, wherein the acquired distribution information includes:

first distribution information acquired by applying addition with a predetermined weight to a plurality of receiving signals acquired by transmitting elastic waves to an object and receiving reflected waves reflected in the object; and second distribution information acquired by applying to the plurality of receiving signals adaptive signal processing with a weight adaptively changing according to the receiving signals, wherein the display method comprises:

receiving information about a user-input depth range, within the object subjected to display of a distribution related to the acoustic characteristics; and displaying, when the depth range is narrower than a predetermined range, an image of the second distribution information or a combined image obtained by combining the first distribution information and the second distribution information for an area corresponding to the depth range.

18. The non-transitory computer-readable storage medium according to claim 17, wherein the program further causes the computer to execute, determining a display enlargement rate for the distribution related to the acoustic characteristics based on a relation between the depth range input by the user and the display area in the screen of the display unit for displaying the distribution related to the acoustic characteristics.

19. The non-transitory computer-readable storage medium according to claim 17, wherein the program further causes the computer to execute displaying, when displaying the image of the second distribution information in the area corresponding to the depth range or the combined image, an image of the first distribution information in a range including at least the area corresponding to the depth range, and a guide for indicating the area corresponding to the depth range in the image of the first distribution information.

20. The non-transitory computer-readable storage medium according to claim 17, wherein the program further causes the computer to selectively execute the following modes:

a first mode in which, upon reception of the information about the depth range, when the depth range is narrower than the predetermined range, the image of the second distribution information in the area corresponding to the depth range or the combined image is displayed; and a second mode in which, upon reception of the information about the depth range, an image of the first distribution information in the area corresponding to the depth range is displayed.

21. An object information acquisition apparatus comprising:

a fixed signal processing unit configured to apply addition with a predetermined weight to a plurality of received signals obtained by receiving echo waves by a plurality of conversion elements to acquire first distribution information;

an adaptive signal processing unit configured to apply to the plurality of received signals adaptive signal processing with a weight adaptively changing according to the receiving signals to acquire second distribution information; and a display control unit configured to output image information for displaying on a display unit an image indicating a distribution related to acoustic characteristics within the object, wherein the display control unit receives information about a user-input depth range, within the object subjected to display of a distribution related to the acoustic characteristics, input by a user, and outputs, when the depth range is narrower than a predetermined range, image information for displaying on the display unit an image of the second distribution information or a combined image obtained by combining the first distribution information and the second distribution information for an area corresponding to the depth range.

* * * * *